United States Patent [19]

Howell

[11] Plant 4,166

[45] Dec. 20, 1977

[54] APPLE TREE

[75] Inventor: Zeb Kenneth Howell, Zillah, Wash.

[73] Assignees: Claud Callahan; Marjorie McCormick, both of Yakima, Wash.

[21] Appl. No.: 742,528

[22] Filed: Nov. 15, 1976

[51] Int. Cl.[2] ..... A01H 5/03

[52] U.S. Cl. ..... Plt./34

[58] Field of Search ..... Plt./34

[56] References Cited

U.S. PATENT DOCUMENTS

P.P. 2,024 2/1961 Jenkins ..... Plt./34

*Primary Examiner*—Robert E. Bagwill

*Attorney, Agent, or Firm*—Frank B. Robb

[57] ABSTRACT

There is disclosed an Apple tree wherein the same comprises a combination of wide angle limb structure, large dark green leaves, golden color apple similar in shape to Starkrimson Red Delicious, smooth russet-free skin, abundant juice when green, early sugar sweet flavor, late harvest ability, long keeping quality in ordinary refrigeration, freeze resistance, firm fruit, high sugar content, exceptional bruise resistance, abundant fruit clusters on long stems and excellent resistance to mildew.

4 Drawing Figures

The present invention relates to a new and distinct variety of Apple tree which was discovered by me as a chance seedling one year old, growing among Starkspur Golden Delicious, U.S. Plant Pat. No. 2,024, and Starkrimson Red Delicious, U.S. Plant Pat. No. 1,565, being a spreading spur type tree and which I denominate as "Firm Gold" and was grown in my orchard in Zillah, Wash.

Inasmuch as this tree was growing among the Starkspur and Starkrimson, and has some of the characteristics of each, the tree was particularly noticed because of the very large size of the leaves which are rather outstanding and dark green in color.

The wide angle limb structure of the seedling was also notable, and when the first crop of fruit was noticed, the long sleek shape of the apple was particularly noticeable as it is more like the Starkrimson in shape than the usual Starkspur Golden Delicious.

The tree was tested by grafting the same over 6-year old Rome trees, and 8-year old Romes which produce the same beautiful type apples which are substantially identical in every respect to those of the parent tree, the propagation of the trees being effected by grafting of which a large number have been prepared for planting in the same orchard as the parent tree with the fruit being observed as identical to that on the parent tree.

Succeeding generations have been grafted, and I am convinced that my new sport is definitely distinguished from its parent trees whichever they may be, as well as from other varieties of apple trees of which I am aware, as evidenced by the following unique combination of principal characteristics which are outstanding in the sport:

1. The continuous ability to produce consistently, and particularly the very large leaves which are substantially larger than those of Starkspur Golden and very dark green as noted.

2. The long, sleek shape of the apple resembling more the Starkrimson Red apple than the usual Starkspur Gold.

3. The white lenticels in contrast to the Starkspur lenticels which are black.

4. The five distinct points which make the apple more resembling the Starkrimson than is usually the case.

5. The very smooth skin which is free of russet.

6. The abundant juice even when the fruit is green, and the early sugar with a sweet flavor before the Starkspur Goldens are comparably ripened.

7. The late harvest habit which is 2 weeks after the Starkspur season, and thus extends the season for Golden Delicious and particularly my variety.

8. The long keeping characteristics of the fruit which have been kept for 14 months under ordinary refrigeration with very little shrivelling, and it is notable that the fruit keeps as well in regular storage as other Golden Delicious do in controlled atmosphere storage.

9. The very distinctive larger and darker pink blossoms than those of Starkspur Golden.

10. The firm fruit, pressure testing at harvest at 19–22½ lbs., sugar testing 11½–13% S.S. as compared to Starkspur Golden which tests 14–16 lbs. with sugar at 10–11% S.S. The firmness preventing easy bruising and contrasting with Starkspur which black marks upon rough handling.

11. The very prolific habit of fruiting which provides that many fruit spurs hold five perfectly formed apples, size 80's–88's because the stems are very long, and the tree on the average will produce fruit averaging 80's to 100's in size.

12. The very resistant habit to mildew of the trees as compared to Starkspur and other apples around, with the buds and blossoms being very freeze resistant.

Asexual reproduction of my new variety through several generations by grafting as performed by me in my orchard at Zillah, Wash., show that the foregoing characteristics and distinctions come true and are established and transmitted through succeeding progagations.

The accompanying drawing showing several branches with the very dense apple growth thereon, and characteristic shape of these apples, is illustrated in one view; the new apple of my variety being illustrated in comparison with the Starkspur Golden in another view, and immediately below the same in section the respective apples compared, with the shape being evident and the points at the end being quite apparent in that view, and a fourth view showing the leaves as compared with the much smaller leaf of the Starkspur Golden U.S. Plant Pat. No. 2,024. The typical foliage and fruit specimens are all depicted in color as nearly true as is reasonable possible to make the same in a color illustration of this character.

The following is a detailed description of my new variety, with color terminology reference being made to the Nickerson Color Fan published by Munsell Color Company, except where general terms of ordinary dictionary significance are applicable:

Locality where grown and observed: Zillah, Wash.

Dates of first and last picking: About October 6 to October 12, with the size, sugar and pressure testing indicating it would be proper to pick about September 30, but the color must become a little more golden in order to have them finish attractively.

Tree: Medium size; vigorous; spreading; dense; vase-formed; rapid growing; hardy; very productive; regular bearer.

*Trunk.*—Stocky; medium smooth.

*Branches.*—Medium; smooth; much-branched.

*Color.*—Green (light olive 7.5Y 5/5).

*Lenticels.*—White; numerous; small.

Foliage:

*Leaves.*—Large; long (from about 5 inches); very wide (2¾ inches); ovate; taper-pointed; thick.

*Color.*—Dark Green (moderate Olive Green 7.5GY 4/4)

*Margin.*—Finely serrate.

*Petiole.*—Length about 1½ inches; medium thickness.

Flowers:

*Dates of first and full bloom.*—About April 26 and April 29 respectively. This is about medium as compared with other varieties.

*Size.*—Large.

*Color.*—Pink.

Fruit:

*Maturity when described.*—Hard and ripe, about October 6.

*Size.*—Uniform; axial diameter about 3¾ inches; transverse diameter about 2¾ inches.

*Form.*—Very uniform; oblong; ovate.

*Cavity.*—Acute. Depth — about ⅝ inches. Breadth — about ½ inch.

*Basin.*—Abrupt; narrow; angular; pubescent.

*Stem.*—Slender caliper. Length — About 1½ inches.

*Bracts.*—Wanting.

*Calyx.*—Closed; segments persistent; narrowly acute; about ⅜ inches long; erect; outer surface pubescent; inner surface pubescent.

*Eye.*—Small.

*Skin.*—Thick; smooth; glossy; waxed. Dots — Obscure; many; small. Color — White. Distribution — Uniform. Ground color — Pale or whitish green. Bloom — wanting. General color effect — Yellow (brilliant greenish yellow 7.5Y 9/8) some blushing.

*Flesh.*—Juicy. Color — White. Texture — Hard; firm; fine; crisp. Flavor — Sweet; sprightly; delicate. Aroma — Pronounced. Quality — Best. Core — Medium. Bundle area — Medium sized; oblate; symmetrical. Halves of core — Equal. Bundles — Yellowish; conspicuous. Alternate bundle — Reaches tube above stamens. Core lines — Clasping; distinct cross section. Carpellary area — Distinct; small size. Calyx tube — Pubescent; funnel formed. Stem of funnel — Long. Depth of tube to shoulder — About ⅜ inch. Entire depth — About ⅝ inch. Styles — Present; united; pubescent. Stamens — In one whorl; median. Axillary cavity — Wanting. Seed cells — Open. Cell walls — Thick; tough. Length — About ⅞ inch. Breadth — About ⅜ inch. Longitudinal section — Narrowly ovate. Surface — Smooth. Cross section — Narrow.

Seeds: 12 perfect; none imperfect; usually about 3 in one cell.

*Length.*—about 5/16 inch.

*Breadth.*—about 3/16 inch.

*Form.*—Acute.

*Color.*—2.5YR 3/3.

Use: Market; dessert; culinary.

Keeping quality: Good; about 300–330 days in ordinary storage.

Disease and insect resistance: Very resistant to mildew as compared to Starkspur and other apples in trees such as Starkrimson which surround one of the trees of the new variety. The buds and blossoms very freeze resistant, as compared with other varieties grown under the same conditions in the area of Zillah, Wash.

I claim:

1. A new and distinct variety of Apple tree, substantially as herein shown and described, characterized particularly as to novelty by the unique combination of wide angle limb structure, large dark green leaves, long sleek shape similar to Starkrimson Red Delicious and as compared to Starkspur Golden Delicious, five distinct points similar to Starkrimson Red Delicious, the smooth skin free of russet, the abundant juice even when the fruit is green, with early sugar sweet flavor before Starkspur Golden but still permitting harvest two weeks after Starkspur, and thus extending harvest season, with ability to keep long in ordinary refrigeration, with blossoms larger and darker pink than Starkspur, with very hardy buds and blossoms being freeze resistant; the fruit being firmer and pressure testing at harvest 19 lbs. to 22½ lbs. and sugar testing 11½–13% S.S., with extreme resistance to bruising and the abundant fruit clusters with long fruit stems, the variety being very resistant to mildew as compared to other known varieties.

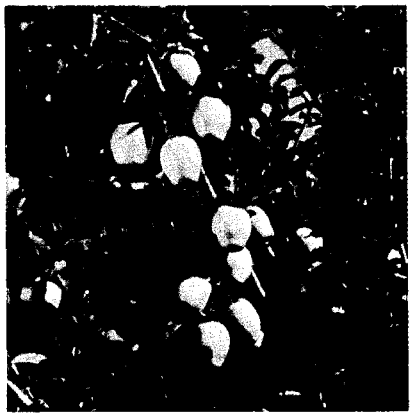
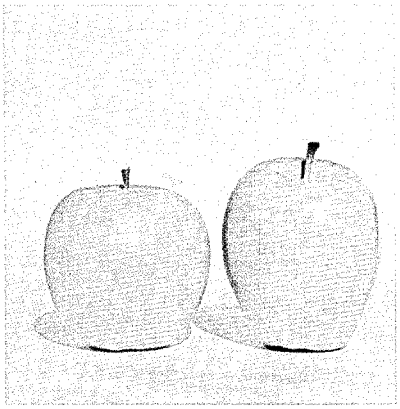
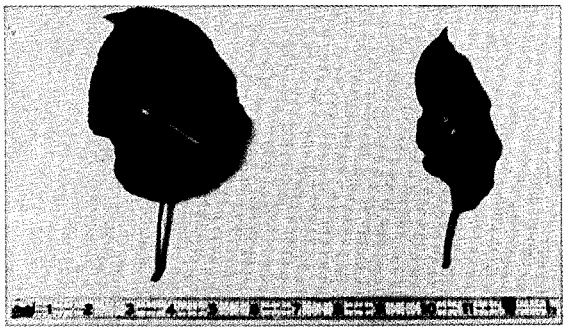
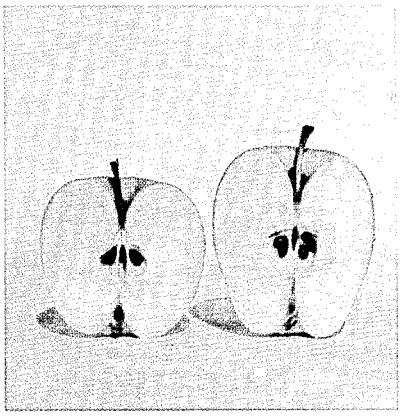

* * * * *